United States Patent
Fujimori

(10) Patent No.: US 10,281,710 B2
(45) Date of Patent: May 7, 2019

(54) IMAGING MODULE AND ENDOSCOPE APPARATUS EACH HAVING A FLEXIBLE SUBSTRATE DIVIDED INTO DIFFERENT REGIONS WHERE A CHIP HAVING A TRANSMISSION BUFFER AND A DRIVE SIGNAL CABLE ARE CONNECTED TO THE DIFFERENT REGIONS

(71) Applicant: OLYMPUS CORPORATION, Tokyo (JP)

(72) Inventor: Noriyuki Fujimori, Suwa (JP)

(73) Assignee: OLYMPUS CORPORATION, Tokyo (JP)

(*) Notice: Subject to any disclaimer, the term of this patent is extended or adjusted under 35 U.S.C. 154(b) by 420 days.

(21) Appl. No.: 15/082,375

(22) Filed: Mar. 28, 2016

(65) Prior Publication Data

US 2016/0209637 A1  Jul. 21, 2016

Related U.S. Application Data

(63) Continuation of application No. PCT/JP2014/070599, filed on Aug. 5, 2014.

(30) Foreign Application Priority Data

Sep. 30, 2013  (JP) .................. 2013-204883

(51) Int. Cl.
*H04N 5/374* (2011.01)
*G02B 23/24* (2006.01)
(Continued)

(52) U.S. Cl.
CPC .......... *G02B 23/2484* (2013.01); *A61B 1/051* (2013.01); *G02B 23/2423* (2013.01);
(Continued)

(58) Field of Classification Search
CPC ............ G02B 23/2484; G02B 23/2476; G02B 23/2423; H04N 7/183; H04N 5/2254;
(Continued)

(56) References Cited

U.S. PATENT DOCUMENTS 4,677,471 A * 6/1987 Takamura ................ A61B 1/05 348/373
6,313,456 B1  11/2001 Miyashita et al.
2002/0080233 A1  6/2002 Irion et al.

FOREIGN PATENT DOCUMENTS

JP  H04-357928 A  12/1992
JP  H10-032747 A  2/1998
(Continued)

OTHER PUBLICATIONS

International Search Report dated Nov. 11, 2014 issued in PCT/JP2014/070599.
(Continued)

*Primary Examiner* — Padma Haliyur
(74) *Attorney, Agent, or Firm* — Scully, Scott, Murphy & Presser, P.C.

(57) ABSTRACT

An imaging module includes: a first chip having a light-receiving unit; a flexible printed board connected to an electrode pad of the first chip via an inner lead extended from one end of the flexible printed board; a second chip having a transmission buffer on the flexible printed board; an image signal cable configured to output an image signal; and a drive signal cable configured to input a drive signal. The first and second chips constitute a CMOS imager. The image signal output from the first chip is amplified by the second chip. The flexible printed board includes two or more regions divided by bending the flexible printed board at a bending part arranged parallel to an optical axis direction of the imaging module. The second chip and the drive signal
(Continued)

cable are connected to different regions of the flexible printed board.

14 Claims, 12 Drawing Sheets

(51) Int. Cl.
*A61B 1/05* (2006.01)
*H04N 5/225* (2006.01)
*H04N 7/18* (2006.01)

(52) U.S. Cl.
CPC ....... *G02B 23/2476* (2013.01); *H04N 5/2253* (2013.01); *H04N 5/2254* (2013.01); *H04N 5/374* (2013.01); *H04N 7/183* (2013.01); *H04N 2005/2255* (2013.01)

(58) Field of Classification Search
CPC ................. H04N 5/2253; H04N 5/374; H04N 2005/2255; A61B 1/051
See application file for complete search history.

(56) References Cited

FOREIGN PATENT DOCUMENTS

| | | |
|---|---|---|
| JP | H10-105395 A | 4/1998 |
| JP | 2000-210252 A | 8/2000 |
| JP | 2002-291693 A | 10/2002 |
| JP | 2010-268077 A | 11/2010 |
| JP | 2011-200340 A | 10/2011 |

OTHER PUBLICATIONS

Extended Supplementary European Search Report dated Mar. 13, 2017 in European Patent Application No. 14 84 7320.0.
Decision to Grant a Patent dated May 29, 2018 in Japanese Patent Application No. 2013-204883.

\* cited by examiner

IMAGING MODULE AND ENDOSCOPE APPARATUS EACH HAVING A FLEXIBLE SUBSTRATE DIVIDED INTO DIFFERENT REGIONS WHERE A CHIP HAVING A TRANSMISSION BUFFER AND A DRIVE SIGNAL CABLE ARE CONNECTED TO THE DIFFERENT REGIONS

CROSS-REFERENCE TO RELATED APPLICATIONS

This application is a continuation of PCT international application Ser. No. PCT/JP2014/070599 filed on Aug. 5, 2014 which designates the United States, incorporated herein by reference, and which claims the benefit of priority from Japanese Patent Application No. 2013-204883, filed on Sep. 30, 2013, incorporated herein by reference.

BACKGROUND

1. Technical Field

The disclosure relates to an imaging module and an endoscope apparatus, the imaging module being provided at a distal end of an insertion unit of an endoscope that is configured to be inserted into a subject to image the inside of the subject.

2. Related Art

Conventionally, endoscope apparatuses have been widely used for various examinations in the medical field and industrial field. Medical endoscope apparatuses from among the above can obtain an in-vivo image in a body cavity by inserting an elongated flexible insertion unit, in which an image sensor is provided at the distal end, in the body cavity of the subject such as a patient without incising the subject. In addition, the medical endoscope apparatuses can treat the subject by projecting a treatment tool from the insertion unit distal end as necessary. Therefore, the medical endoscope apparatuses have been widely used.

An imaging unit is fit into the insertion unit distal end of this endoscope apparatus, and a signal cable is soldered to an FPC board of the imaging unit. The imaging unit includes an image sensor and a flexible printed board (referred to as an FPC board below) such as a tape automated bonding (TAB) on which electronic components such as a capacitor and an IC chip included in a drive circuit of the image sensor are mounted.

The imaging unit can be easily become larger by the increase in the number of mounting electronic components and signal cables according to the increase in the number of the pixels in the image sensor. In contrast, a technique has been proposed in which an FPC board is bent to realize a small-sized imaging unit (for example, refer to JP 2000-210252 A and JP 2010-268077 A).

SUMMARY

In some embodiments, an imaging module a includes: a first chip having at least a light receiving unit in which a plurality of pixels for generating and outputting an imaging signal according to a light receiving amount is arranged in two-dimensional matrix and a reading unit configured to select a target pixel from among the plurality of pixels to read the imaging signal; a flexible printed board connected to an electrode pad of the first chip via an inner lead extended from one end of the flexible printed board; a second chip having at least a transmission buffer mounted on the flexible printed board; and a signal cable having an image signal cable to which an image signal is output and having a drive signal cable configured to input a drive signal, the image signal cable and the drive signal cable being connected to the other end of the flexible printed board. The first and second chips constitute a CMOS image sensor, and the image signal output from the first chip is amplified by the second chip. The flexible printed board includes two or more regions divided by bending the flexible printed board by at least one bending part which is arranged in parallel to an optical axis direction of the imaging module. The second chip and the drive signal cable are connected to different regions of the flexible printed board.

In some embodiments, an endoscope apparatus includes an insertion unit, a distal end of which the imaging module is provided.

The above and other features, advantages and technical and industrial significance of this invention will be better understood by reading the following detailed description of presently preferred embodiments of the invention, when considered in connection with the accompanying drawings.

DETAILED DESCRIPTION

As modes for carrying out the invention (hereinafter referred to as "embodiment(s)"), an endoscope apparatus having an imaging module will be described below. The invention is not limited to the embodiments. The same reference signs are used to designate the same elements throughout the drawings. The drawings are schematic diagrams, and a relationship between thickness and width of each member, a ratio of each member, and the like are different from those in reality. Also, a figure includes a part having the dimensions and ratio different from those of other figures.

First Embodiment

Figure 1:
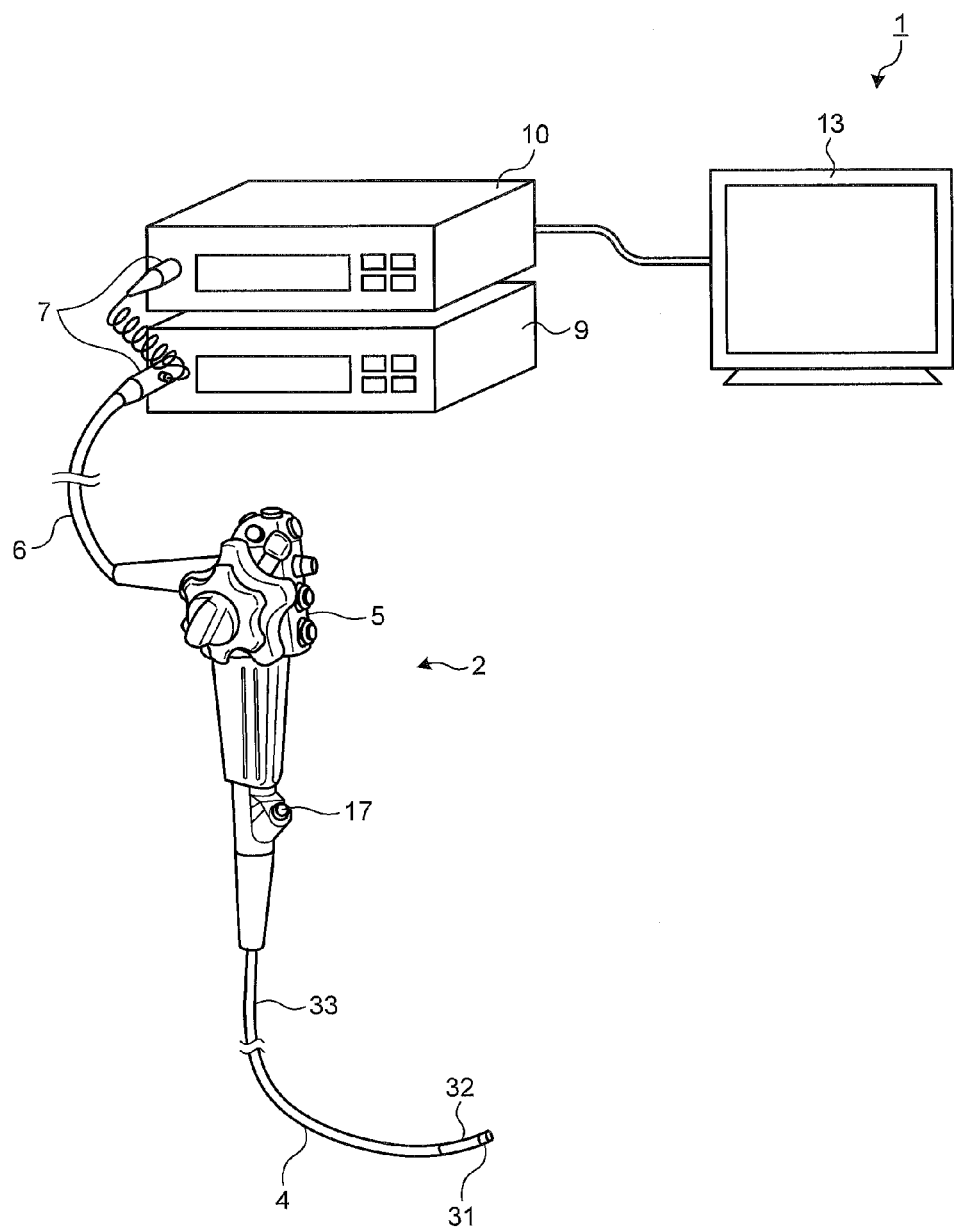
FIG. 1 is a schematic diagram of an overall structure of an endoscope system according to a first embodiment of the present invention.

FIG. 1 is a schematic diagram of an overall structure of an endoscope system according to a first embodiment of the present invention. As illustrated in FIG. 1, an endoscope apparatus 1 includes an endoscope 2, a universal cord 6, a connector 7, a light source device 9, a processor (controller) 10, and a display device 13.

The endoscope 2 captures an in-vivo image of a subject by inserting an insertion unit 4 in a body cavity of the subject and outputs an image signal. An electric cable bundle in the universal cord 6 is extended to a distal end of the insertion unit 4 of the endoscope 2 and connected to an imaging device provided at a distal end part 31 of the insertion unit 4.

The connector 7 is provided at a proximal end of the universal cord 6 and is connected to the light source device 9 and the processor 10. The connector 7 performs predetermined signal processing on the image signal output by the imaging device of the distal end part 31 connected to the universal cord 6 and performs analog-to-digital conversion (A/D conversion) on the image signal and outputs the converted signal.

The light source device 9 is formed of, for example, a white LED. Pulsed white light lighted by the light source device 9 becomes the illumination light emitted from the distal end of the insertion unit 4 of the endoscope 2 to an object via the connector 7 and the universal cord 6.

The processor 10 performs predetermined image processing on the image signal output from the connector 7 and controls the entire endoscope apparatus 1. The display device 13 displays the image signal to which the processing is performed by the processor 10.

An operating unit 5 is connected to a side of the proximal end of the insertion unit 4 of the endoscope 2. In the operating unit 5, various buttons, knobs, and the like for operating endoscope functions are provided. A treatment tool insertion hole 17 is provided in the operating unit 5, and treatment tool such as a living body forceps, an electric scalpel, and an inspection probe is inserted to the body cavity of the subject through the treatment tool insertion hole 17.

The insertion unit 4 includes the distal end part 31 in which the imaging device is provided, a curved part 32 which is continuously provided on the side of the proximal end of the distal end part 31 and can be curved in a plurality of directions, and a flexible tube part 33 which is continuously provided on the side of the proximal end of the curved part 32. The curved part 32 is curved by an operation of a curving operation knob provided in the operating unit 5 and can be curved in four directions, i.e., upwards, downwards, rightwards, and leftwards by pulling and relaxing the curved wire which has been inserted into the insertion unit 4.

A light guide bundle (not illustrated) for transmitting the illumination light from the light source device 9 is arranged in the endoscope 2, and an illumination lens (not illustrated) is arranged at an emission end of the illumination light transmitted by the light guide bundle. The illumination lens is provided in the distal end part 31 of the insertion unit 4, and the illumination light is emitted to the subject.

Figure 2:
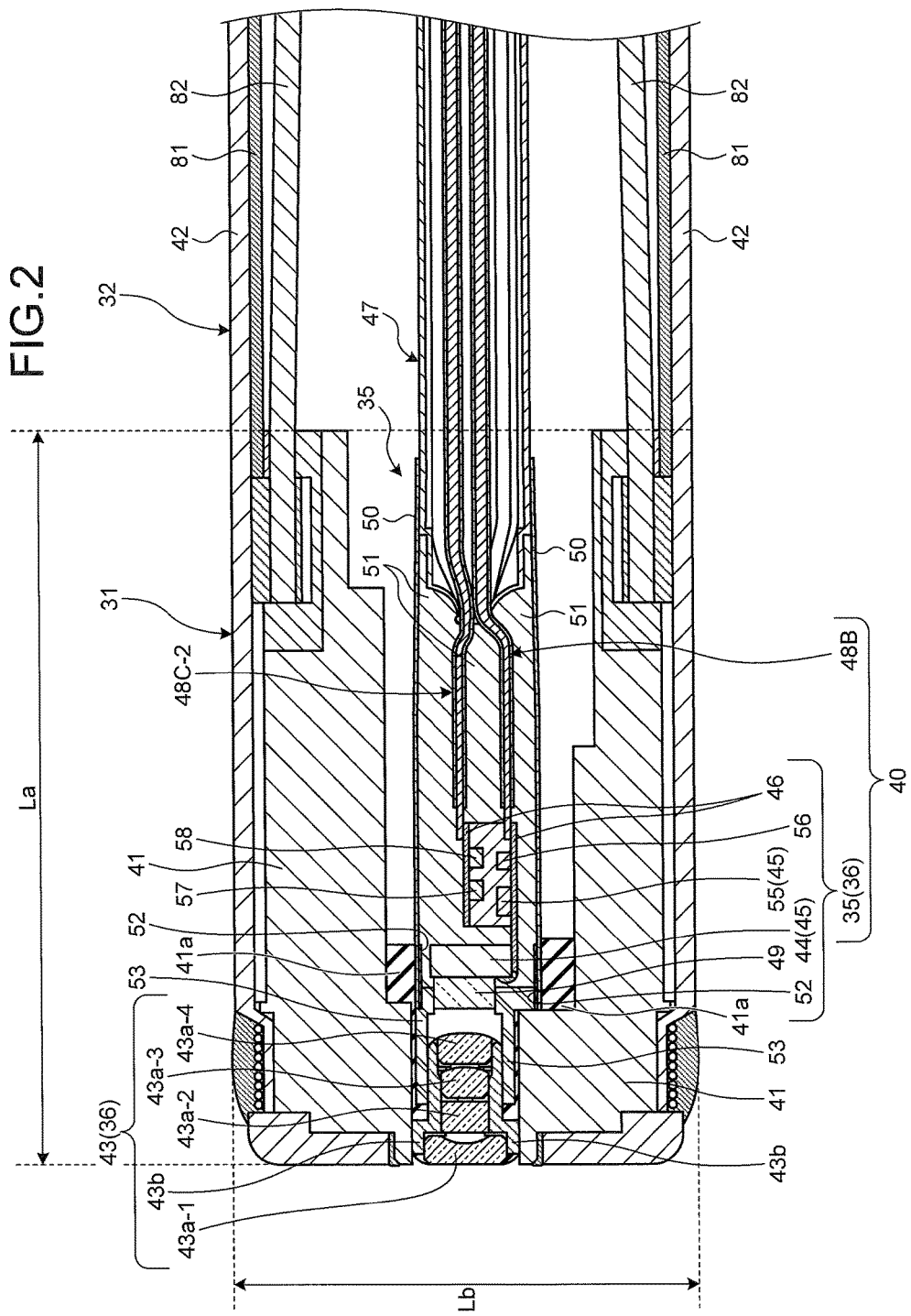
FIG. 2 is a partial cross-sectional view of a distal end of the endoscope illustrated in FIG. 1.

Next, a structure of the distal end part 31 of the endoscope 2 will be described in detail. FIG. 2 is a partial cross-sectional view of a distal end of the endoscope 2. FIG. 2 is a cross-sectional view of a case where the endoscope 2 is cut by a surface perpendicular to a substrate surface of the imaging module provided at the distal end part 31 of the endoscope 2 and a surface parallel to an optical axis direction of the imaging module. The distal end part 31 of the insertion unit 4 of the endoscope 2 and a part of the curved part 32 are illustrated in FIG. 2.

As illustrated in FIG. 2, the curved part 32 can be curved in the four directions, i.e., upwards, downwards, rightwards, and leftwards by pulling and relaxing a curved wire 82 which has been inserted into a curved tube 81 arranged in a coated tube 42 to be described. An imaging device 36 is provided in the distal end part 31 extended to a side of the distal end of the curved part 32.

The imaging device 36 includes a lens unit 43 and an imaging unit 35 arranged on the side of the proximal end of the lens unit 43 and is bonded to the inside of a distal end part body 41 with an adhesive 41a. The distal end part body 41 is formed of a hard member to form an inner space where the imaging unit 35 is housed. A proximal end outer peripheral part of the distal end part body 41 is covered with the flexible coated tube 42. A member on the proximal end side from the distal end part body 41 is formed of a flexible member so that the curved part 32 can be curved. The distal end part 31 in which the distal end part body 41 is arranged is a hard part of the insertion unit 4. The length La of the hard part is from the distal end of the insertion unit 4 to the proximal end of the distal end part body 41. The length Lb corresponds to an outside diameter of the distal end of the insertion unit 4.

The lens unit 43 includes a plurality of objective lenses 43a-1 to 43a-4 and a lens holder 43b which holds the objective lenses 43a-1 to 43a-4. The lens unit 43 is fixed to the distal end part body 41 by inserting and fixing the distal end of the lens holder 43b in the distal end part body 41.

The imaging unit 35 includes a CMOS imager 45 which has a first chip 44 which has a light receiving surface for receiving the light on its surface and a second chip 55 which has at least a transmission buffer, a flexible printed board (FPC board) 46 which is extended from the first chip 44, electronic components 56 to 58 which are mounted on the FPC board, and a glass lid 49 which is bonded to the first chip 44 to cover the light receiving surface of the first chip 44.

Figure 3:
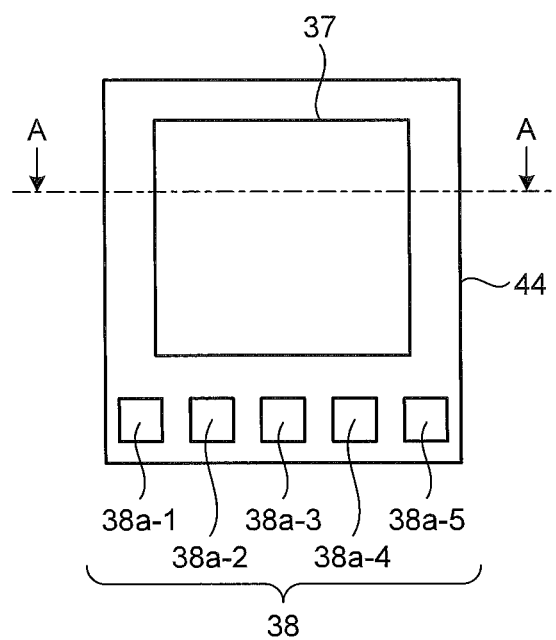
FIG. 3 is a front view of a light receiving surface of a first chip in FIG. 2.
Figure 4:
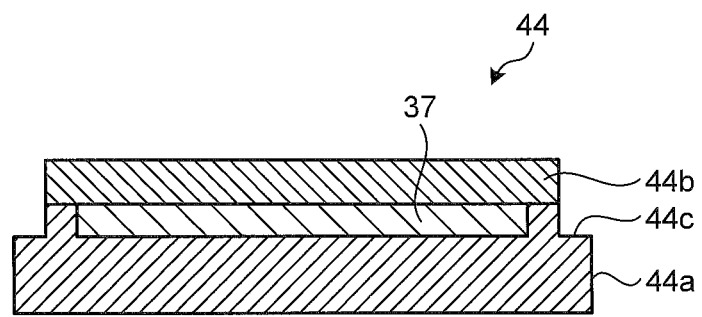
FIG. 4 is a cross-sectional view taken along the line A-A of FIG. 3.
Figure 5:
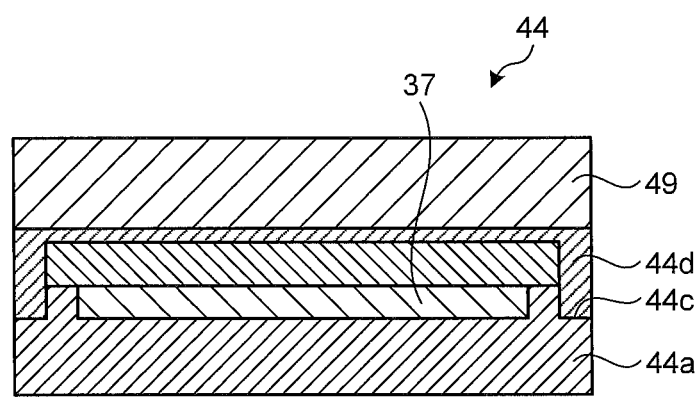
FIG. 5 is a cross-sectional view of a connection surface of the first chip to a glass lid.

As illustrated in FIG. 3, a light receiving unit 37 in which a plurality of pixel units is arranged in two-dimensional matrix and an electrode pad 38 are formed on the side of the light receiving surface of the first chip 44, and the first chip 44 includes a reading unit (not illustrated) which reads an imaging signal photoelectrically converted by the light receiving unit 37. As illustrated in FIG. 4, in the first chip 44, a wiring layer including an insulating Low-k film 44b may be formed on a surface of a base material 44a so as to cover the light receiving unit 37. The Low-k film is formed of SiOC, SiOF, or resin and has a low permittivity. Therefore, a speed of a signal transmission in the wiring layer can be enhanced. However, there is a problem in that water is easily penetrated and a water resistance (moisture resistance) is low. Accordingly, when the Low-k film is formed, it is preferable to provide a step-cut part 44c on an outer peripheral surface of the first chip 44 in order to prevent corrosion of wirings and separation of the Low-k film caused by the penetration of the water into the first chip 44. When the step-cut part 44c is provided on the outer peripheral surface of the first chip 44 as illustrated in FIG. 5, an extra sealing resin 44d which is used when the glass lid 49 is connected to the first chip 44 is coated, and the sealing resin 44d is fixed to the step-cut part 44c so as to be protruded. Then, the Low-k film 44b can be sealed. Accordingly, the penetration of the water into the first chip 44 can be prevented, and reliability can be improved. When the Low-k film 44b is sealed and the glass lid 49 is connected to the first chip 44 with the sealing resin 44d at the same time, it is preferable to use a material with a high transmittance for visible light and a low moisture permeability as the sealing resin 44d. Also, the Low-k film 44b may be sealed in a different process and by using a different material from those of the connection between the glass lid 49 and the first chip 44.

As illustrated in FIG. 3, the electrode pad 38 is formed under the light receiving unit 37 of the first chip 44 (when the Low-k film 44b is formed on the surface of the base material 44a, the Low-k film 44b is formed in a lower layer of the electrode pad 38). The electrode pad 38 includes a drive signal electrode pad 38a-1, power supply signal electrode pads 38a-2 and 38a-3, a ground electrode pad 38a-4, and an image signal electrode pad 38a-5. The drive signal electrode pad 38a-1 and the image signal electrode pad 38a-5 are arranged so as to be separated farthest from each other. The drive signal electrode pad 38a-1, the power supply signal electrode pads 38a-2 and 38a-3, the ground electrode pad 38a-4, and the image signal electrode pad 38a-5 are respectively and electrically connected to an inner lead 39a-1, an inner lead 39a-2, an inner lead 39a-3, an inner lead 39a-4, and an inner lead 39a-5 (refer to FIG. 8). The inner lead 39a-1 transmits a drive signal, and the inner lead 39a-2 transmits a ground signal. The inner lead 39a-3 and the inner lead 39a-4 transmit power signals, and the inner lead 39a-5 transmits the image signal. A connection part between the electrode pad 38 and an inner lead 39 is covered with a sealing resin 54b, and the first chip 44 is connected to the FPC board 46.

A connection part between the first chip 44 and the FPC board 46 is covered with a metal reinforced member 52. In order to prevent an influence of external static electricity relative to the second chip 55 and the electronic components 56 to 58 on the FPC board 46, the reinforced member 52 is provided apart from the first chip 44 and the FPC board 46.

An imaging module 40 includes the imaging device 36 having the lens unit 43 and the imaging unit 35, a drive signal cable 48A which is electrically connected to the first chip 44 to drive the first chip 44, an image signal cable 48B which transmits the image signal output from the first chip 44, power supply signal cables 48C-1 and 48C-2 which supply power to the first chip 44, the second chip 55, and the electronic components 56 to 58, and includes a ground signal cable 48D.

Proximal ends of the drive signal cable 48A, the image signal cable 48B, the power supply signal cables 48C-1 and 48C-2, and the ground signal cable 48D are bundled by an electric cable bundle 47 and are extended in a direction towards the proximal end of the insertion unit 4. The electric cable bundle 47 is arranged and inserted into the insertion unit 4 and is extended to the connector 7 via the operating unit 5 and the universal cord 6 illustrated in FIG. 1.

An object image formed by the objective lenses 43a-1 to 43a-4 of the lens unit 43 is detected by the first chip 44 arranged at an image forming position of the objective lenses 43a-1 to 43a-4 and is converted into an image signal.

An outer peripheries of the distal end parts of the imaging unit 35 and the electric cable bundle 47 are covered with heat-shrinkable tubes 50 to improve resistance. Gaps between the components in the heat-shrinkable tube 50 and the FPC board 46 are filled with adhesive resin 51.

First chip holders 53 hold the first chip 44 bonded to the glass lid 49 by engaging the outer peripheral surface of the glass lid 49 with an inner peripheral surfaces of the first chip holders 53 on the side of the proximal end. An outer peripheral surface on the side of the proximal end of the first chip holder 53 is engaged with the inner peripheral surface on the side of the distal end of the reinforced member 52. An outer peripheral surface on the side of the proximal end of the lens holder 43b is engaged with the inner peripheral surface on the side of the distal end of the first chip holder 53. In a state where the members are engaged with each other in this way, the outer peripheral surface of the lens holder 43b, the outer peripheral surface of the first chip holder 53, and the outer peripheral surface on the side of the distal end of the heat-shrinkable tube 50 are fixed to the inner peripheral surface of the distal end of the distal end part body 41 with the adhesive 41a.

Figure 6:
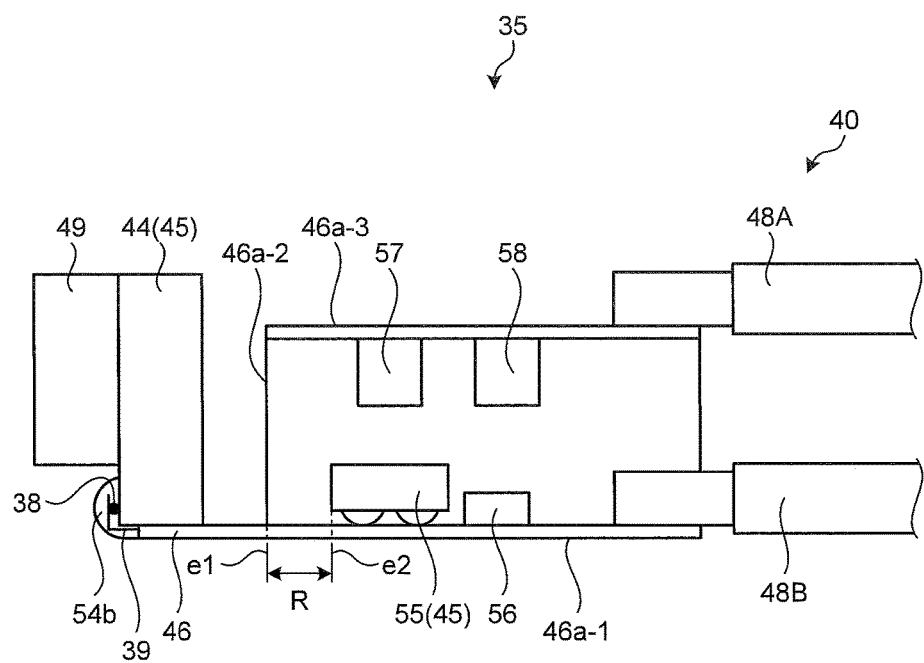
FIG. 6 is a plan view of a side surface of the imaging module in FIG. 2 on a side of an aperture of a flexible printed board.
Figure 7:
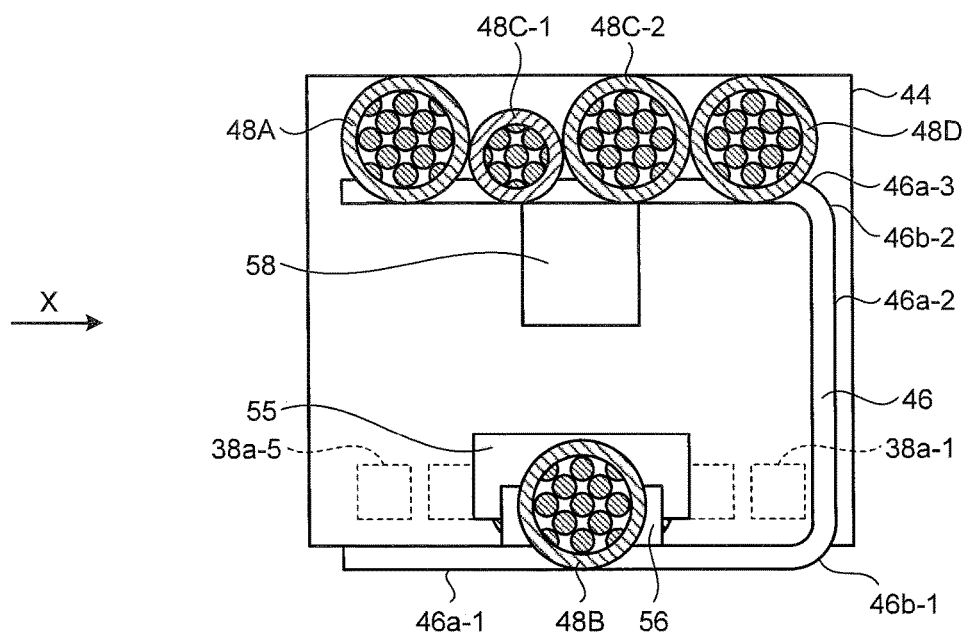
FIG. 7 is a plan view of the imaging module in FIG. 2 viewed from a side of a rear end.
Figure 8:
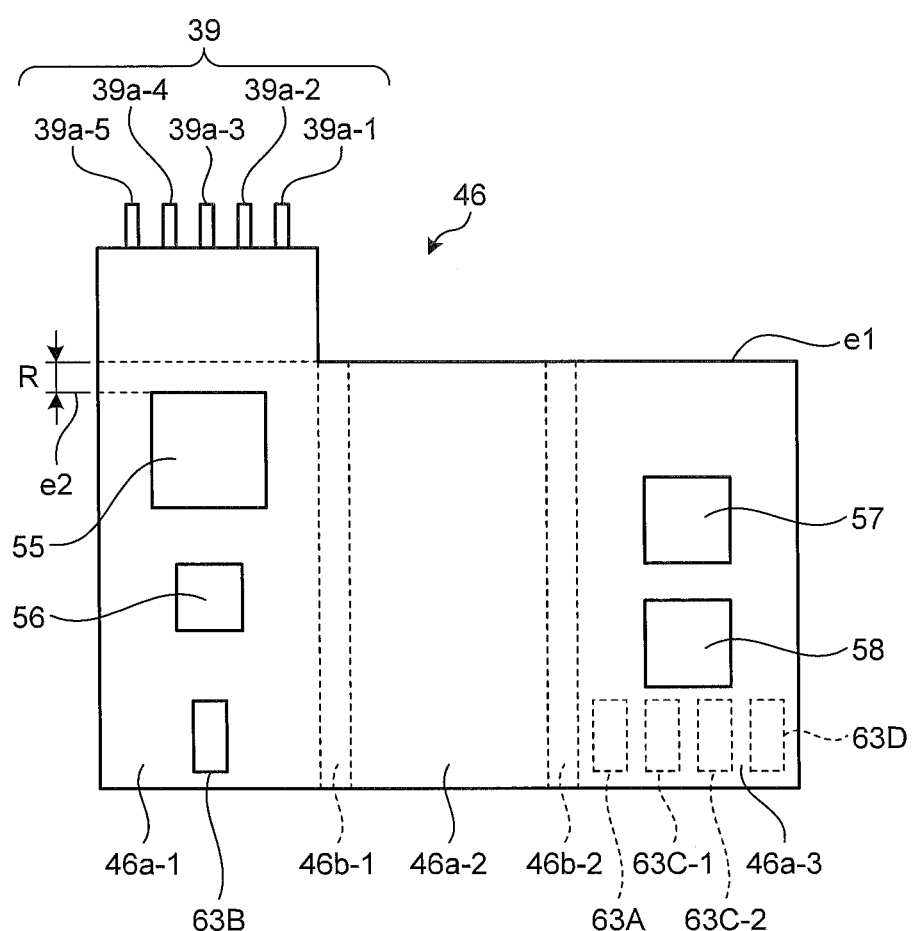
FIG. 8 is a development view of the flexible substrate in FIG. 2.
Figure 9:
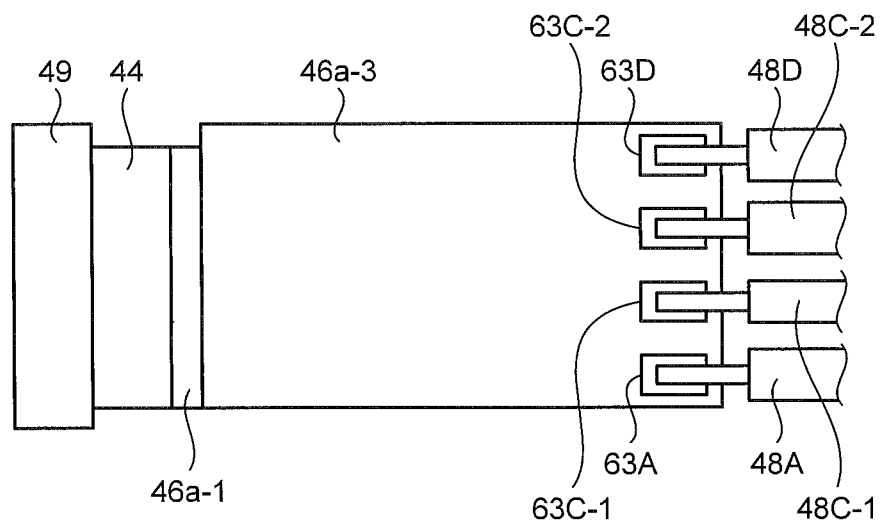
FIG. 9 is a plan view of the imaging module in FIG. 2 viewed from the top.
Figure 10:
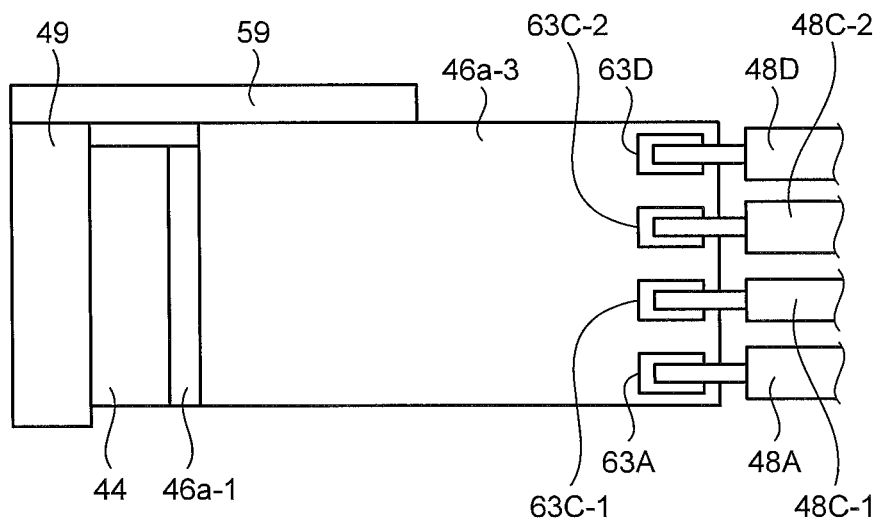
FIG. 10 is a plan view of a case where a reinforced part has been formed on the imaging module viewed from the top.

Next, the imaging module 40 will be described. FIG. 6 is a plan view of a side surface of the imaging module in FIG. 2 viewed from a side of the aperture of the flexible printed board (in a direction of an arrow X in FIG. 7). FIG. 7 is a plan view of the imaging module in FIG. 2 viewed from a side of a rear end. FIG. 8 is a development view of the flexible substrate in FIG. 2. FIG. 9 is a plan view of the imaging module in FIG. 2 viewed from the top. FIG. 10 is a plan view of an imaging module of a case where a reinforced part has been formed viewed from the top.

The FPC board 46 includes a first region 46a-1 which is extended from the electrode pad 38 of the first chip 44 in a direction opposite to where the light receiving surface is provided, a second region 46a-2 which is formed on a right side of the first region 46a-1 in the width direction and in parallel to the first region 46a-1, and a third region 46a-3 which is formed parallel to a side of the second region 46a-2 opposite to where the second region 46a-2 contacts with the first region 46a-1. A first bending part 46b-1 is formed between the first region 46a-1 and the second region 46a-2, and a second bending part 46b-2 is formed between the second region 46a-2 and the third region 46a-3. The FPC board 46 is formed in a C shape by bending the first bending part 46b-1 and the second bending part 46b-2 so that the regions are perpendicular to each other. The first bending part 46b-1 and the second bending part 46b-2 are formed to be thinner than the other regions or a slit is formed in a part of each of the first bending part 46b-1 and the second bending part 46b-2 so that the first bending part 46b-1 and the second bending part 46b-2 can be easily bent.

The second chip 55 and the electronic component 56 are mounted on the first region 46a-1 of the FPC board 46, and the electronic components 57 and 58 are mounted on the third region 46a-3. A connection land 63B for connecting the image signal cable is formed on the mounting surfaces of the second chip 55 and the like on the first region 46a-1, and connection lands 63A, 63C-1, 63C-2, and 63D are formed on the rear side of the mounting surface of the electronic components 57 and 58 on the third region 46a-3. The connection lands 63A, 63C-1, 63C-2, and 63D respectively connect the drive signal cable 48A, the power supply cables 48C-1 and 48C-2, and the ground signal cable 48D.

In order to hold the FPC board 46 in a C shape, the gaps in the FPC board 46 are filled with the adhesive resin 51. However, the FPC board 46 may be held in a C shape by winging a member in the FPC board 46 as a core.

In the first embodiment, the image signal is transmitted from the image signal electrode pad 38a-5 of the first chip 44 to the FPC board 46 via the inner lead 39a-5 and is transmitted to the second chip 55 mounted on the first region 46a-1. After being amplified by the second chip 55 which includes at least the transmission buffer, the image signal is output to the processor 10 via an image signal wiring pattern on the first region 46a-1 and the image signal cable 48B. The image signal output from the image signal electrode pad 38a-5 is weak and easily affected by the noise. However, the imaging module 40 according to the first embodiment can output the weak signal to the second chip and amplify it in the shortest time by mounting the second chip 55 on the first region extended from the first chip 44. Therefore, an image noise caused by crosstalk of the drive signal is hardly generated. To reduce the effect of the noise, it is preferable that the image signal wiring pattern be linearly formed (so that the length becomes shorter).

On the other hand, the drive signal input from the drive signal cable 48A connected to the third region 46a-3 is input to the drive signal electrode pad 38a-1 mainly via a drive signal wiring pattern formed on the third region. It is preferable that the drive signal wiring pattern be wired from the connection part to the drive signal cable 48A which is on the rear end side of the third region 46a-3 to the front side of the third region (a side of the first chip 44) and be wired from the third region 46a-3 to the first region 46a-1 via the second region 46a-2 in a region R between a front end part e1 of the third region 46a-3 and a first chip side e2 of the second chip 55. The drive signal is transmitted mainly via the drive signal wiring pattern formed on the third region 46a-3, that is, the drive signal is separated from the image signal on the side of the first chip 44 than the second chip 55 and transmitted into different regions. Therefore, the effect of the crosstalk to the image signal by the drive signal can be reduced.

The whole of the imaging module 40, including the FPC board 46, the second chip 55, the electronic components 56 to 58, the drive signal cable 48A, the image signal cable 48B, the power supply signal cables 48C-1 and 48C-2, and the ground signal cable 48D, is arranged within a projection region where the first chip 44 is projected in the optical axis direction. FIG. 9 is a plan view of the imaging module 40 viewed from the top. As illustrated in FIG. 9, one end of the glass lid 49 in the width direction and one end of the second region 46a-2 of the FPC board 46 are formed on a single surface. The imaging module 40 can be easily held even if the imaging module 40 is small in size by forming the width directions of the glass lid 49 and/or the first chip 44 and the second region 46a-2 of the FPC board 46 on the single surface. In addition, as illustrated in FIG. 10, on the surface of both, a plate-shaped reinforced part 59 may be bonded with an adhesive. The imaging module 40 can be easily held by forming the reinforced part 59, and a connection strength between the glass lid 49, the first chip 44, and the FPC board 46 can be increased by the adhesive for bonding the reinforced part 59.

In the first embodiment, the drive signal electrode pad 38a-1 and the image signal electrode pad 38a-5 are formed to be separated farthest from each other, and the third region 46a-3 connected to the drive signal cable 48A is formed on the side of the drive signal electrode pad 38a-1 of the first region 46a-1. Therefore, the drive signal wiring pattern can reduce the crosstalk to the image signal by the drive signal without intersecting with the image signal wiring pattern.

In the first embodiment, the drive signal cable 48A, the power supply signal cables 48C-1 and 48C-2, and the ground signal cable 48D are connected to the outside surface of the third region 46a-3 (opposite side to where the electronic components 57 and 58 are mounted). However, they may be mounted on the inside surface of the third region 46a-3 (the surface same as the mounting surface of the electronic components 57 and 58). As long as the whole of the imaging module 40 is arranged within the projection region where the first chip 44 is projected in the optical axis direction, the image signal cable 48B may be connected to the outside surface of the first region 46a-1 (opposite side to where the second chip 55 is mounted). Similarly, if there are a plurality of drive signals and image output signals, the cables may be connected to the first region and the third region.

Second Embodiment

An imaging module according to a second embodiment is different from the first embodiment in that an FPC board 46 is formed in a U shape and a second region 46a-2 which is formed in parallel to an end face (right side) of a first region 46a-1 in the width direction is connected to a drive signal cable 48A.

Figure 11:
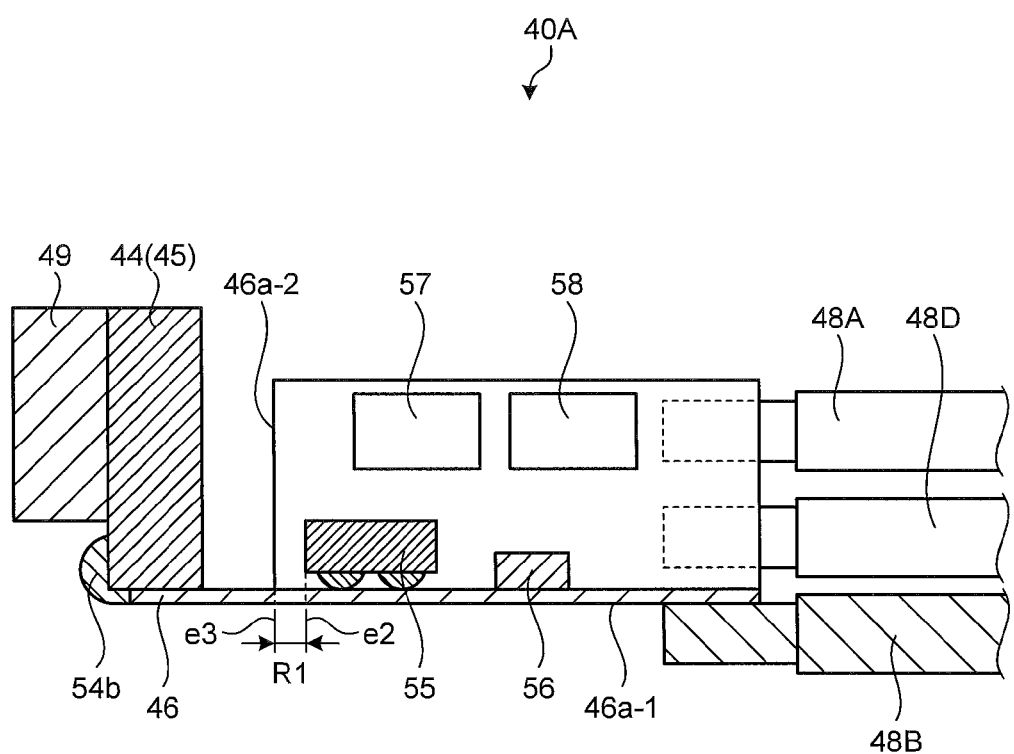
FIG. 11 is a cross-sectional view of an imaging module according to a second embodiment.
Figure 12:
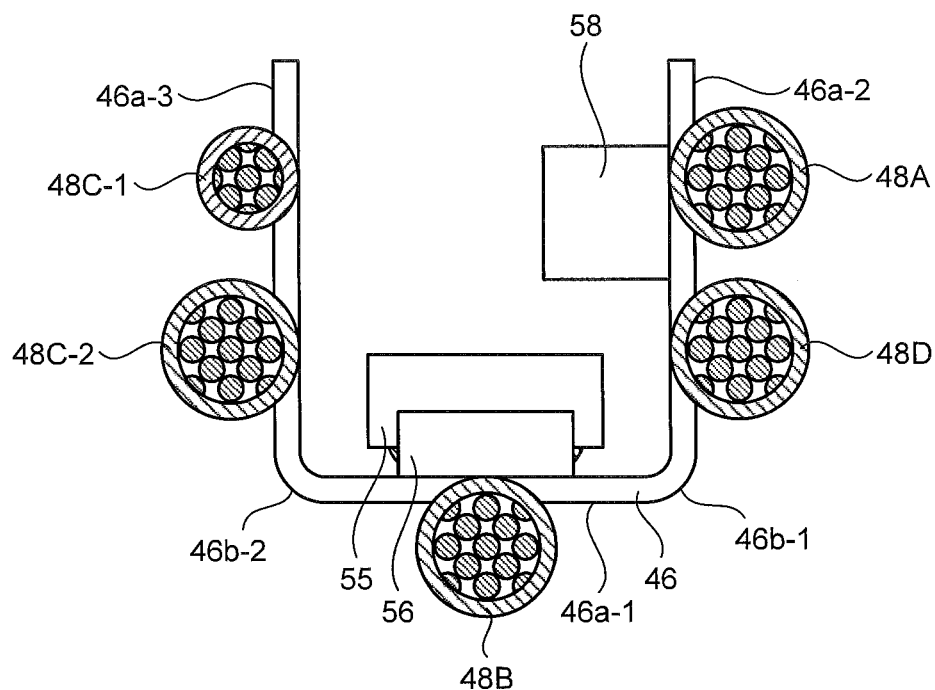
FIG. 12 is a plan view of the imaging module in FIG. 11 viewed from a side of a rear end.

FIG. 11 is a cross-sectional view of a case where the imaging module according to the second embodiment is cut by a surface vertical to a surface of a flexible printed board and in parallel to an optical axis direction of the imaging module. FIG. 12 is a plan view of the imaging module in FIG. 11 viewed from a side of a rear end. In FIG. 12, a first chip 44 is not shown.

In an imaging module 40A according to the second embodiment, a flexible printed board 46 includes the first region 46a-1 which is extended from an electrode pad 38 of the first chip 44, the second region 46a-2 which is formed in parallel to the right side of the first region 46a-1, and a third region 46a-3 which is formed in parallel to the left side of the first region 46a-1. A first bending part 46b-1 and a second bending part 46b-2 are respectively formed between the first region 46a-1 and the second region 46a-2 and between the first region 46a-1 and the third region 46a-3. The FPC board 46 is formed in the U shape by bending the first bending part 46b-1 and the second bending part 46b-2 so that the regions are perpendicular to each other.

In the second embodiment, a second chip 55 and an electronic component 56 are formed on the first region 46a-1 of the FPC board 46, and electronic components 57 and 58 are mounted on the second region 46a-2. An image signal cable 48B is connected to the outside surface of the first region 46a-1 of the FPC board 46 (rear surface side of the mounting surface of the second chip 55), and a drive signal cable 48A and a ground signal cable 48D are connected to the outside surface of the second region 46a-2 (rear surface side of the mounting surface of the electronic components 57 and 58). Also, power supply signal cables 48C-1 and 48C-2 are connected to the outside surface of the third region 46a-3.

Similarly to the first embodiment, an image signal is transmitted from an image signal electrode pad 38a-5 of the first chip 44 to the FPC board 46 via an inner lead 39a-5 and is transmitted to the second chip 55 mounted on the first region 46a-1. After being amplified by the second chip 55, the image signal is output to a processor 10 via an image signal wiring pattern on the first region 46a-1 and the image signal cable 48B.

On the other hand, the drive signal input from the drive signal cable 48A connected to the second region 46a-2 is input to the drive signal electrode pad 38a-1 mainly via a drive signal wiring pattern formed on the second region 46a-2. It is preferable that the drive signal wiring pattern be arranged from a connection part to the drive signal cable 48A which is on the rear end side of the second region 46a-2 to the front side of the second region (on a side of the first chip 44) and be arranged from the second region 46a-2 to the first region 46a-1 in a region R1 between a front end part e3 of the second region 46a-2 and a side position e2 of the second chip 55 on a side of the first chip 44. In the second embodiment, the drive signal is transmitted mainly via the drive signal wiring pattern formed on the second region, that is, the drive signal is separated from the image signal on the side of the first chip 44 than the second chip 55 and transmitted into different regions. Therefore, the effect of crosstalk to the image signal by the drive signal can be reduced.

Also, in the second embodiment, similarly to the first embodiment, the drive signal electrode pad 38a-1 and the image signal electrode pad 38a-5 are formed to be separated farthest from each other, and the second region 46a-2 connected to the drive signal cable 48A is formed on the side of the drive signal electrode pad 38a-1 of the first region 46a-1. Therefore, the drive signal wiring pattern can reduce the crosstalk to the image signal by the drive signal without intersecting with the image signal wiring pattern.

Third Embodiment

Figure 13:
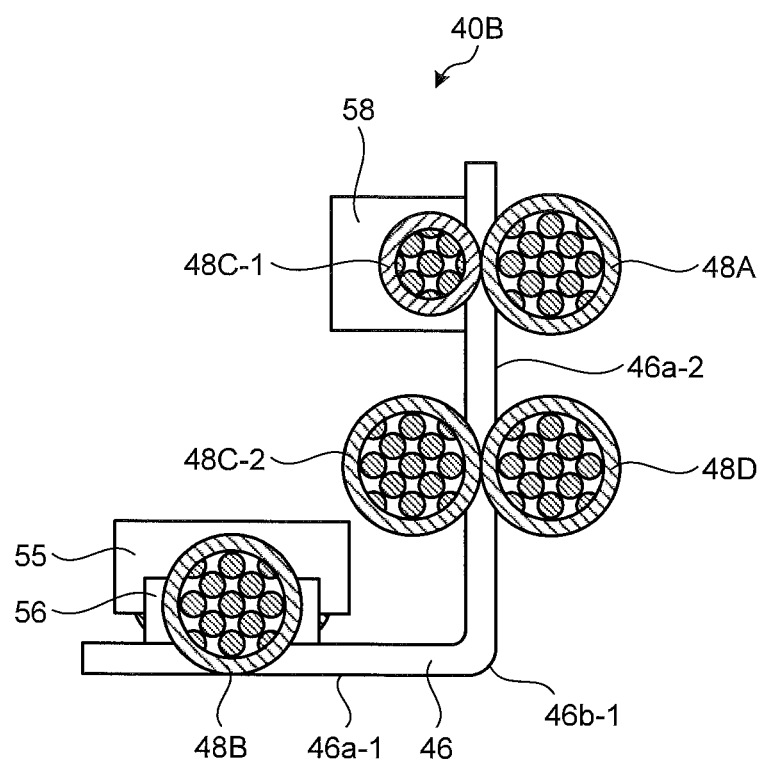
FIG. 13 is a cross-sectional view of an imaging module according to a third embodiment.

An imaging module according to a third embodiment is different from the first embodiment in that an FPC board 46 is formed in an L shape and a second region 46a-2 which is formed in parallel to an end face of a first region 46a-1 in the width direction is connected to a drive signal cable 48A. FIG. 13 is a plan view of the imaging module according to the third embodiment viewed from a side of a rear end. In FIG. 13, a first chip 44 is not shown.

In an imaging module 40B according to the third embodiment, the flexible printed board 46 includes the first region 46a-1 which is extended from an electrode pad 38 of the first chip 44 and the second region 46a-2 which is formed in parallel to the right side of the first region 46a-1. A bending part 46b-1 between the first region 46a-1 and the second region 46a-2 is bent so that the first region 46a-1 and the second region 46a-2 are perpendicular to each other.

In the third embodiment, a second chip 55 and an electronic component 56 are mounted on the first region 46a-1 of the FPC board 46, and electronic components 57 and 58 are mounted on the second region 46a-2. An image signal cable 48B is connected to the inside surface of the first region 46a-1 of the FPC board 46 (a mounting surface of the second chip 55), and a drive signal cable 48A and a ground signal cable 48D are connected to the outside surface of the second region 46a-2 (opposite side to where the electronic components 57 and 58 are mounted). Power supply signal cables 48C-1 and 48C-2 are connected to the inside surface of the second region 46a-2.

Similarly to the first embodiment, an image signal is transmitted from an image signal electrode pad 38a-5 of the first chip 44 to the FPC board 46 via an inner lead 39a-5 and is transmitted to the second chip 55 mounted on the first region 46a-1. After being amplified by the second chip 55, the image signal is output to a processor 10 via an image signal wiring pattern on the first region 46a-1 and the image signal cable 48B. On the other hand, similarly to the second embodiment, the drive signal input from the drive signal cable 48A connected to the second region 46a-2 is input to the drive signal electrode pad 38a-1 mainly via a drive signal wiring pattern formed on the second region 46a-2. It is preferable that the drive signal wiring pattern be arranged from a connection part to the drive signal cable 48A which is on the rear end side of the second region 46a-2 to the front side of the second region 46a-2 (on a side of the first chip 44) and be arranged from the second region 46a-2 to the first region 46a-1 in a region between a front end part of the second region 46a-2 and a side position of the second chip 55 on a side of the first chip. In the third embodiment, the drive signal is transmitted mainly via the drive signal wiring pattern formed on the second region, that is, the drive signal is separated from the image signal on the side of the first chip 44 than the second chip 55 and transmitted into different regions. Therefore, the effect of crosstalk to the image signal by the drive signal can be reduced.

Also, in the third embodiment, similarly to the first embodiment, the drive signal electrode pad 38a-1 and the image signal electrode pad 38a-5 are formed to be separated farthest from each other, and the second region 46a-2 connected to the drive signal cable 48A is formed on the side of the drive signal electrode pad 38a-1 of the first region 46a-1. Therefore, the drive signal wiring pattern can reduce the effect on the image signal without intersecting with the image signal wiring pattern.

Fourth Embodiment

Figure 14:
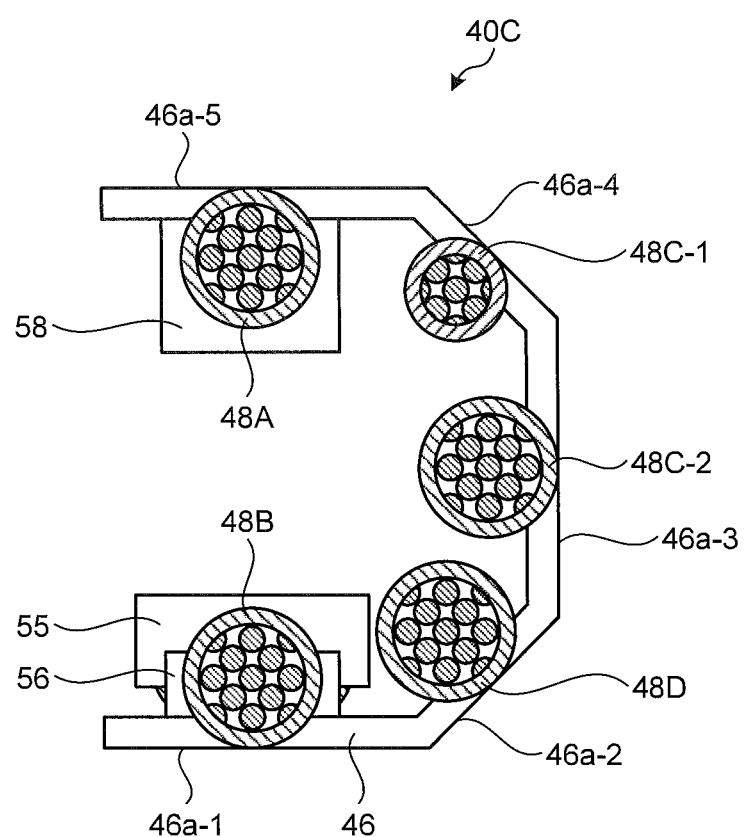
FIG. 14 is a cross-sectional view of an imaging module according to a fourth embodiment.

An imaging module according to a fourth embodiment is different from the first embodiment in that an FPC board 46 includes five regions and a drive signal cable 48A is connected to a fifth region 46a-5 which is the farthest from a first region 46a-1 connected to an image signal cable 48B. FIG. 14 is a plan view of the imaging module according to the fourth embodiment viewed from a side of a rear end. In FIG. 14, a first chip 44 is not shown.

In an imaging module 40C according to the fourth embodiment, the flexible printed board 46 includes the first region 46a-1 which is extended from an electrode pad 38 of the first chip 44, the second region 46a-2 which is formed in parallel to the first region 46a-1 on the right side of the first region 46a-1, a third region 46a-3 which is formed parallel to a side of the second region 46a-2 opposite to where second region 46a-2 contacts with the first region 46a-1, a fourth region 46a-4 which is formed parallel to a side of the third region 46a-3 opposite to where the third region 46a-3 contacts with the second region 46a-2, and the fifth region 46a-5 which is formed parallel to a side of the fourth region 46a-4 opposite to where the fourth region 46a-4 contacts with the third region 46a-3. Bending parts are respectively formed between the first region 46a-1 and the second region 46a-2, between the second region 46a-2 and the third region 46a-3, between the third region 46a-3 and the fourth region 46a-4, and between the fourth region 46a-4 and the fifth region 46a-5. The FPC board 46 has substantially an arc shape by bending the board at each bending part.

In the fourth embodiment, a second chip 55 and an electronic component 56 are formed on the first region 46a-1 of the FPC board 46, and electronic components 57 and 58 are mounted on the fifth region 46a-5. The image signal cable 48B is connected to the inside surface of the first region 46a-1 of the FPC board 46 (the mounting surface of the second chip 55), and the drive signal cable 48A is connected to the inside surface of the fifth region 46a-5 (the mounting surface of the electronic components 57 and 58). A ground signal cable 48D is connected to the inside surface of the second region 46a-2, and a power supply signal cable 48C-2 is connected to the inside surface of the third region 46a-3, and a power supply signal cable 48C-1 is connected to the inside surface of the fourth region 46a-4.

Similarly to the first embodiment, an image signal is transmitted from an image signal electrode pad 38a-5 of the first chip 44 to the FPC board 46 via an inner lead 39a-5 and is transmitted to the second chip 55 mounted on the first region 46a-1. After being amplified by the second chip 55, the image signal is output to a processor 10 via an image signal wiring pattern on the first region 46a-1 and the image signal cable 48B. On the other hand, the drive signal input from the drive signal cable 48A connected to the fifth region 46a-5 is input to the drive signal electrode pad 38a-1 mainly via a drive signal wiring pattern formed on the fifth region. The drive signal wiring pattern is wired from a connection part to the drive signal cable 48A which is on a side of the rear end of the fifth region 46a-5 to the front side of the fifth region 46a-5 (a first chip 44 side) and is wired to the first region 46a-1 via the fourth region 46a-4, the third region 46a-3, and the second region 46a-2 in a region between a front end part of the fifth region 46a-5 and a side surface position of the first chip in the second chip 55. In the fourth embodiment, the drive signal is transmitted mainly via the drive signal wiring pattern formed on the fifth region, that is, the drive signal is separated from the image signal on the side of the first chip 44 than the second chip 55 and transmitted into different regions. Therefore, the effect of crosstalk to the image signal by the drive signal can be reduced.

Also, in the fourth embodiment, similarly to the first embodiment, the drive signal electrode pad 38a-1 and the image signal electrode pad 38a-5 are formed to be separated farthest from each other, and the fifth region 46a-5 connected to the drive signal cable 48A is formed on the side of the drive signal electrode pad 38a-1 of the first region 46a-1. Therefore, the drive signal wiring pattern can reduce the effect on the image signal without intersecting with the image signal wiring pattern.

According to some embodiments, among regions divided by bending an FPC board, a drive signal cable is connected to a region different from a region where a second chip for amplifying an image signal is mounted. With this structure, it is possible to reduce interference between the image signal and a drive signal and thereby to prevent noise.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging module comprising:
   a first chip having at least a plurality of pixels for generating and outputting an imaging signal according to a light receiving amount, the plurality of pixels being arranged in two-dimensional matrix;
   a flexible printed board connected to an electrode pad of the first chip via an inner lead extended from one end of the flexible printed board;
   a second chip having at least a transmission buffer mounted on the flexible printed board; and
   a signal cable having an image signal cable to which an image signal is output and having a drive signal cable configured to input a drive signal, the image signal cable and the drive signal cable being connected to the other end of the flexible printed board, wherein
   the first and second chips constitute a CMOS image sensor, and the image signal output from the first chip is amplified by the second chip,
   the flexible printed board includes two or more regions divided by bending the flexible printed board by at least one bending part which is arranged in parallel to an optical axis direction of the imaging module, and
   the second chip and the drive signal cable are connected to different regions of the flexible printed board, wherein:
   the flexible printed board includes a first region extending from the electrode pad of the first chip, and a second region formed parallel to one of end faces of the first region in a width direction,
   the flexible printed board is bent at the bending part between the first and second regions such that the first region is perpendicular to the second region, and
   the second chip and the image signal cable are connected to the first region, and the drive signal cable is connected to the second region.

2. The imaging module according to claim 1, wherein a drive signal wiring pattern for transmitting the drive signal is arranged from the second region to the first region between the second chip and an end face of the second region on a side of the first chip.

3. An imaging module comprising:
   a first chip having at least a plurality of pixels for generating and outputting an imaging signal according to a light receiving amount, the plurality of pixels being arranged in two-dimensional matrix;
   a flexible printed board connected to an electrode pad of the first chip via an inner lead extended from one end of the flexible printed board;
   a second chip having at least a transmission buffer mounted on the flexible printed board; and
   a signal cable having an image signal cable to which an image signal is output and having a drive signal cable configured to input a drive signal, the image signal cable and the drive signal cable being connected to the other end of the flexible printed board, wherein
   the first and second chips constitute a CMOS image sensor, and the image signal output from the first chip is amplified by the second chip,
   the flexible printed board includes two or more regions divided by bending the flexible printed board by at least one bending part which is arranged in parallel to an optical axis direction of the imaging module, and
   the second chip and the drive signal cable are connected to different regions of the flexible printed board, wherein
   the flexible printed board includes a first region extending from the electrode pad of the first chip, a second region formed parallel to one of end faces of the first region in a width direction, and a third region formed parallel to a side of the second region opposite to where the second region contacts with the first region,
   the flexible printed board is bent at bending parts between the first and second regions and between the second and third regions such that the first and second regions are perpendicular to each other and the second and third regions are perpendicular to each other, and
   the second chip and the image signal cable are connected to the first region, and the drive signal cable is connected to the third region.

4. The imaging module according to claim 3, wherein a drive signal wiring pattern for transmitting the drive signal is arranged from the third region to the first region between the second chip and an end face of the third region on a side of the first chip.

5. An imaging module comprising:
a first chip having at least a plurality of pixels for generating and outputting an imaging signal according to a light receiving amount, the plurality of pixels being arranged in two-dimensional matrix;
a flexible printed board connected to an electrode pad of the first chip via an inner lead extended from one end of the flexible printed board;
a second chip having at least a transmission buffer mounted on the flexible printed board; and
a signal cable having an image signal cable to which an image signal is output and having a drive signal cable configured to input a drive signal, the image signal cable and the drive signal cable being connected to the other end of the flexible printed board, wherein
the first and second chips constitute a CMOS image sensor, and the image signal output from the first chip is amplified by the second chip,
the flexible printed board includes two or more regions divided by bending the flexible printed board by at least one bending part which is arranged in parallel to an optical axis direction of the imaging module, and
the second chip and the drive signal cable are connected to different regions of the flexible printed board, wherein
the flexible printed board includes a first region extending from the electrode pad of the first chip, a second region formed parallel to one of end faces of the first region in a width direction, and a third region formed parallel to the other of the end faces of the first region in the width direction,
the flexible printed board is bent at bending parts between the first and second regions and between the first and third regions such that the first and second regions are perpendicular to each other, and the first and third regions are perpendicular to each other, and
the second chip and the image signal cable are connected to the first region, and the drive signal cable is connected to the second region or the third region.

6. The imaging module according to claim 5, wherein a drive signal wiring pattern for transmitting the drive signal is arranged from the second region or the third region to the first region between the second chip and an end face of the second region or the third region connected to the drive signal cable on a side of the first chip.

7. An imaging module comprising:
a first chip having at least a plurality of pixels for generating and outputting an imaging signal according to a light receiving amount, the plurality of pixels being arranged in two-dimensional matrix;
a flexible printed board connected to an electrode pad of the first chip via an inner lead extended from one end of the flexible printed board;
a second chip having at least a transmission buffer mounted on the flexible printed board; and
a signal cable having an image signal cable to which an image signal is output and having a drive signal cable configured to input a drive signal, the image signal cable and the drive signal cable being connected to the other end of the flexible printed board, wherein
the first and second chips constitute a CMOS image sensor, and the image signal output from the first chip is amplified by the second chip,
the flexible printed board includes two or more regions divided by bending the flexible printed board by at least one bending part which is arranged in parallel to an optical axis direction of the imaging module, and
the second chip and the drive signal cable are connected to different regions of the flexible printed board, wherein
the flexible printed board includes a first region extending from the electrode pad of the first chip and three or more regions formed parallel to an end face of the first region in a width direction,
the flexible printed board is bent at bending parts between the regions such that an outer periphery of the flexible printed board has a polygonal shape or a combination of a polygonal shape and an arc shape, and
the second chip and the image signal cable are connected to the first region, and the drive signal cable is connected to a region of the three or more regions farthest from the first region.

8. The imaging module according to claim 7, wherein a drive signal wiring pattern for transmitting the drive signal is arranged from the connected region to the first region between the second chip and an end face of the region farthest from the first region on a side of the first chip.

9. The imaging module according to claim 1, wherein
the electrode pad on the first chip includes at least a drive signal electrode pad and an image signal electrode pad,
the drive signal electrode pad and the image signal electrode pad are arranged separately from each other, and
a region to which the drive signal cable is connected is formed on the first region on a side of the drive signal electrode pad.

10. An endoscope apparatus comprising an insertion unit, the imaging module according to claim 1 is provided at a distal end of the insertion unit.

11. The imaging module according to claim 1, wherein the second chip and the image signal cable are connected to a same region of the flexible printed board.

12. An endoscope apparatus comprising an insertion unit, the imaging module according to claim 3 is provided at a distal end of the insertion unit.

13. An endoscope apparatus comprising an insertion unit, the imaging module according to claim 5 is provided at a distal end of the insertion unit.

14. An endoscope apparatus comprising an insertion unit, the imaging module according to claim 7 is provided at a distal end of the insertion unit.

* * * * *